US007011676B2

(12) United States Patent
Dong

(10) Patent No.: US 7,011,676 B2
(45) Date of Patent: Mar. 14, 2006

(54) FLAT KNITTED STENT AND METHOD OF MAKING THE SAME

(75) Inventor: Qing Dong, Oakland, NJ (US)

(73) Assignee: Scimed Life Systems, Inc., Maple Grove, MN (US)

( * ) Notice: Subject to any disclaimer, the term of this patent is extended or adjusted under 35 U.S.C. 154(b) by 410 days.

(21) Appl. No.: 10/235,447

(22) Filed: Sep. 5, 2002

(65) Prior Publication Data

US 2004/0049260 A1 Mar. 11, 2004

(51) Int. Cl.
*A61F 2/06* (2006.01)
(52) U.S. Cl. .................. 623/1.15; 623/1.5; 623/1.51
(58) Field of Classification Search ............... 623/1.15, 623/1.13, 1.5–1.53
See application file for complete search history.

(56) References Cited

U.S. PATENT DOCUMENTS

| | | | |
|---|---|---|---|
| 3,578,028 A | 5/1971 | Roberts | |
| 4,015,451 A | 4/1977 | Gajjar | |
| 4,193,137 A | 3/1980 | Heck | |
| 4,563,382 A | 1/1986 | Viel | |
| 5,354,309 A | 10/1994 | Schnepp-Pesch et al. | |
| 5,366,504 A | 11/1994 | Andersen et al. | |
| 5,395,390 A | 3/1995 | Simon et al. | |
| 5,397,359 A | 3/1995 | Mittelmeier et al. | |
| 5,569,273 A | 10/1996 | Titone et al. | |
| 5,591,222 A | 1/1997 | Susawa et al. | |
| 5,601,907 A | 2/1997 | Matsumoto | |
| 5,662,713 A | 9/1997 | Andersen et al. | |
| 5,674,276 A | 10/1997 | Andersen et al. | |
| 5,733,327 A | 3/1998 | Igaki et al. | |
| 5,876,445 A | 3/1999 | Andersen et al. | |
| 6,045,568 A | 4/2000 | Igaki et al. | |
| 6,080,177 A | 6/2000 | Igaki et al. | |
| 6,089,051 A | 7/2000 | Gorywoda et al. | |
| 6,146,416 A | 11/2000 | Andersen et al. | |
| 6,161,399 A | 12/2000 | Jayaraman | |
| 6,221,099 B1 | 4/2001 | Andersen et al. | |
| 6,221,100 B1 | 4/2001 | Strecker | |
| 6,241,757 B1 | 6/2001 | An et al. | |
| 6,276,178 B1 | 8/2001 | West et al. | |
| 6,305,436 B1 | 10/2001 | Andersen et al. | |
| 6,355,070 B1 | 3/2002 | Andersen et al. | |
| 6,383,216 B1 | 5/2002 | Kavteladze et al. | |

(Continued)

FOREIGN PATENT DOCUMENTS

EP 1 055 757 A1 11/2000

(Continued)

OTHER PUBLICATIONS

"The Karl Mayer Guide to Technical Textiles", Karl Mayer Textilmaschinenfabrik GmbH, Germany, 2000.

(Continued)

*Primary Examiner*—(Jackie) Tan-Uyen T. Ho
(74) *Attorney, Agent, or Firm*—Hoffmann & Baron, LLP

(57) ABSTRACT

A knitted implantable stent having a hollow tubular structure having opposed open ends defining a wall portion therebetween is provided. The wall portion includes an open lattice structure of a plurality of interconnected perimetrically bound cells. The cells are defined by a plurality cell segments. The cell segments are defined by at least two wires knittingly interlaced in a plurality of loops. Adjacent cell segments are knittingly interlaced with each other to form the open lattice structure of interconnected perimetrically bound cells. The stent may be a singular tubular structure or may be a bifurcated stent. Methods for producing the flat knitted stents include the use of double needle bar flat knitting machines.

35 Claims, 7 Drawing Sheets

U.S. PATENT DOCUMENTS

| | | |
|---|---|---|
| 2001/0003801 A1 | 6/2001 | Strecker |
| 2001/0018609 A1 * | 8/2001 | Smith .................... 623/1.13 |
| 2002/0035396 A1 | 3/2002 | Heath |

FOREIGN PATENT DOCUMENTS

| | | |
|---|---|---|
| WO | WO 92/02301 | 2/1992 |
| WO | WO 92/15342 | 9/1992 |
| WO | WO 96/11720 | 4/1996 |
| WO | WO99/21506 | 5/1999 |
| WO | WO01/12256 | 2/2001 |
| WO | WO02/22049 | 3/2002 |
| WO | WO02/26046 | 5/2002 |

OTHER PUBLICATIONS

Spencer, David J.; "Knitting Technology"; Woodhead Publishing Limited, England; pp. 322-327; 2001.

* cited by examiner

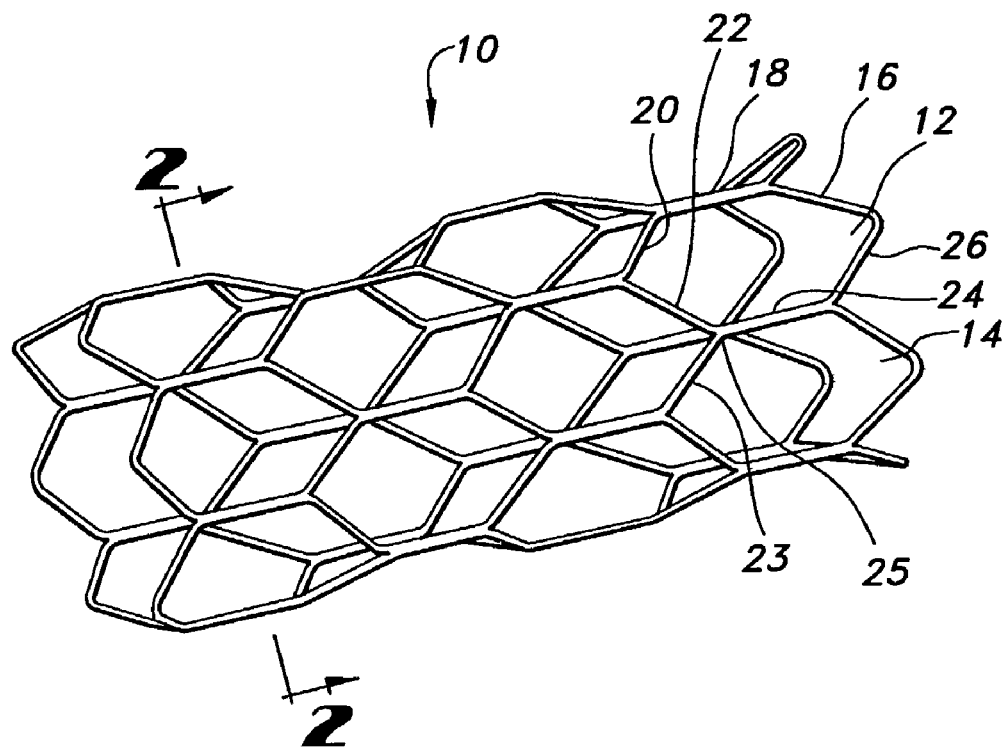
FIG. 1
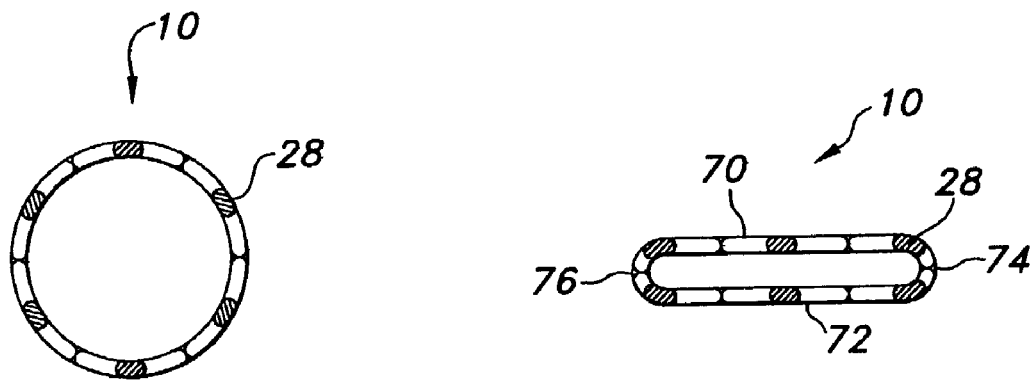
FIG. 2　　　FIG. 3

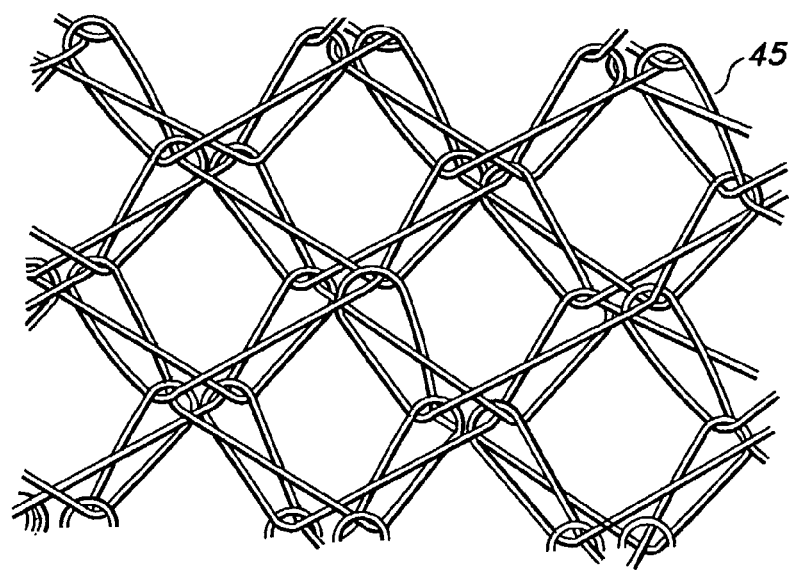
FIG. 7
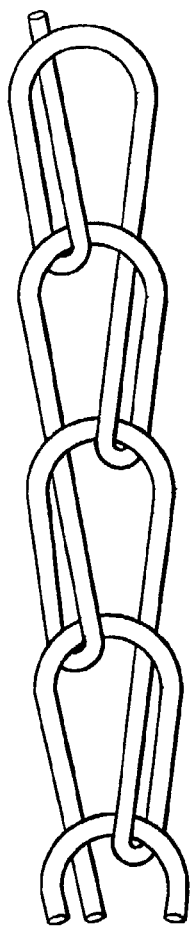
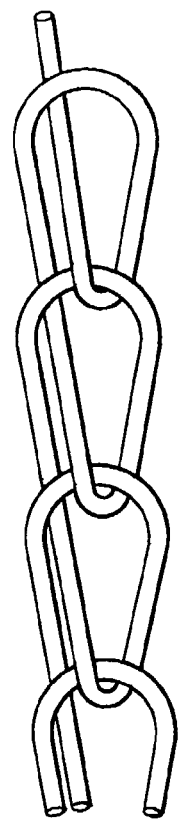
FIG. 8  FIG. 9

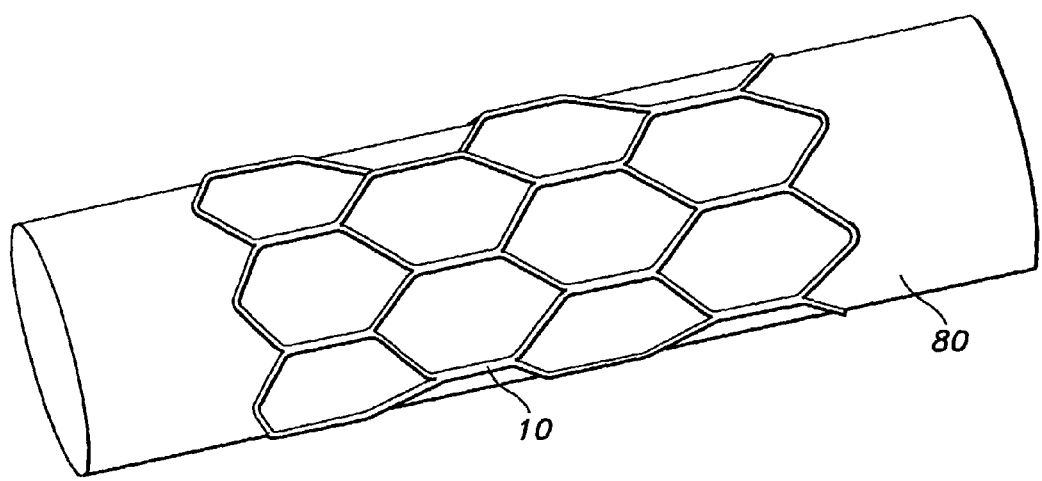
FIG. 13
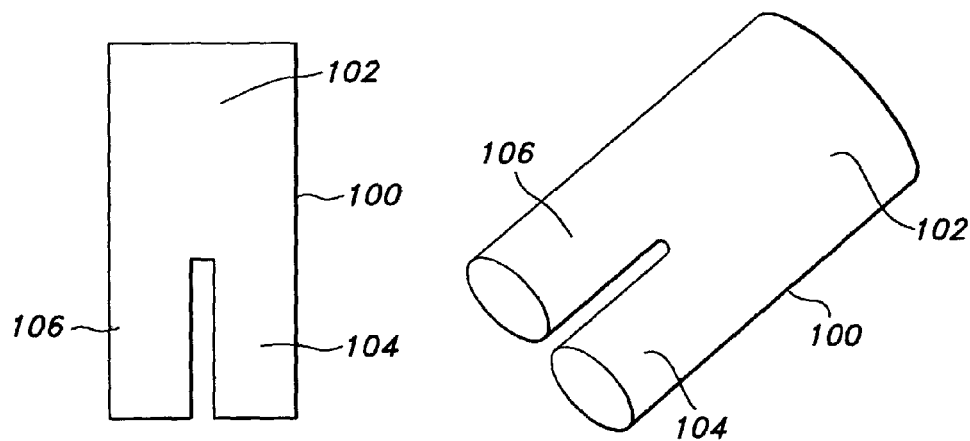
FIG. 12A  FIG. 12B

FLAT KNITTED STENT AND METHOD OF MAKING THE SAME

FIELD OF INVENTION

The present invention relates generally to a knitted tubular implantable stent. More particularly, the present invention relates to a warp knitted stent having an open lattice structure produced on a double needle bar warp knitting machine.

BACKGROUND OF RELATED TECHNOLOGY

An intraluminal prosthesis is a medical device used in the treatment of diseased body vessels, including blood vessels. An intraluminal prosthesis is typically used to repair, replace, or otherwise correct a diseased or damaged blood vessel. An artery or vein may be diseased in a variety of different ways. The prosthesis may therefore be used to prevent or treat a wide variety of defects such as stenosis of the vessel, thrombosis, occlusion or an aneurysm.

One type of intraluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract, bile duct, esophagus, trachea, colon, biliary tract, urinary tract, prostrate and the brain, as well as in a variety of other applications in the body. Endovascular stents have become widely used for the treatment of stenosis, strictures and aneurysms in various blood vessels. These devices are implanted within the vessel to open and/or reinforce collapsing or partially occluded sections of the vessel.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern. Examples of various stent configurations are shown in U.S. Pat. Nos. 4,503,569 to Dotter; 4,733,665 to Palmaz; 4,856,561 to Hillstead; 4,580,568 to Gianturco; 4,732,152 to Wallsten; 5,395,390 to Simon et al., 5,234,457 to Andersen et al. and 4,886,062 to Wiktor.

Stents have been formed from a variety of techniques. For example, a stent made be made from a wire by winding or braiding the wire around a mandrel into a complex configuration, welding the wire at certain junctions, and heat treating the wire to create the implantable stent device. Alternatively, a stent may be made from a tube or sheet by stamping, cutting or etching a pattern into the starting material, expanding and/or rolling the starting material into a suitable stent shape, and heat treating to create the final device. Furthermore, stents can be produced by deposition, such as vapor deposition or electrochemical deposition, of metal onto a cylindrical mold. In addition to these methods stents have been made by knitting wires onto a cylindrical mandrel through use of a circular knitting machine.

Excluding the helically wound coil springs, these various stent configurations have an open lattice structure where the lattice segments are a single wire or single metallic structure. Different lattice segments from one structure may be welded to lattice segments from another structure to form the stent. For example, U.S. Pat. No. 5,395,390 to Simon et al. describes a stent formed from a single wire where the wire is arranged is a plurality of hexagonal cells. Abutting portions of the hexagonal cells are welded to one and the other for form the stent. Such placement of the wire to form the hexagonal cells and the selective welding are complicated and costly manufacturing processes.

One possible way to avoid the need for welding portions of a wire stent to form the stent's open lattice structure is to circularly knit a wire into an open lattice configuration. For example, U.S. Pat. No. 5,234,457 discloses a stent formed from a series of loosely-interlocked knitted wires. The knitted wires define the open lattice structure of the so-formed stent. The different segments forming the open lattice structure are straight laced wires without any interlooping of the wire along intermediate portions of the segments.

All of these manufacturing techniques, however, are quite complicated, making the resulting stent difficult and costly to produce. For example, to produce bifurcated stents, which have two branch stent portions extending from a main stent portion, individual stent portions are produced by the above-described methods and are subsequently and mechanically joined together. Alternatively, bifurcated stents have been produced by circular braiding or circular knitting techniques by forming the main stent portion on a mandrel, removing the stent from and mandrel, transferring the removed stent and the wire spools used to form the stent to a different circular braiding or circular knitting machine, spooling one set of wires into the machine to produce a branched stent portion on its corresponding mandrel and spooling another set of wires into the machine to produce a branched stent portion on its corresponding mandrel. While this latter technique avoids the problem of mechanically joining different stent portions, the required use of different mandrels about which different stent portions must be produced complicate the manufacturing of such stents. Similar complex manufacturing problems even exist even for producing a stent that has just a variable shape, such as a contoured stent or a stent with a varying diameter.

Moreover, stents having their individual lattice cells being formed from a single wire or member have somewhat limited flexibility to vary their shape, or can vary one dimension, such as diameter, only at the expense of another dimension, such as length. For example, stents are often radially expanded during implantation into a bodily lumen. The stents have an open lattice configuration so that the figuration can be somewhat altered to permit, among other things, the radial expansion of the stent. Such changes in the open lattice configuration typically result in a foreshortening of the stent upon expansion because the individual segments forming the lattice are rather unyielding.

Thus, there is a need for a stent having an open lattice structure with increased flexibility without the disadvantages of the prior art. Furthermore, there is a need for a method for producing varying shaped stents, including bifurcated stents, as unitary structures without the complex and complicated techniques associated with the prior art.

SUMMARY OF THE INVENTION

The present invention is a flat knitted stent of unitary knitting structure with an open lattice structure. Due to its knitted construction, the stent of the present invention has enhanced flexibility over stents, including circular knitted stents, of the prior art.

In one aspect of the present invention, a knitted implantable stent including a hollow tubular structure having opposed open ends defining a wall portion therebetween is provided. The wall portion comprises an open lattice structure of a plurality of interconnected perimetrically bound cells. The cells are defined by a plurality cell segments. The cell segments are defined by at least two wires knittingly interlaced in a plurality of loops. Adjacent cell segments are knittingly interlaced with each other to form the open lattice structure of interconnected perimetrically bound cells. The stent may be a singular tubular structure or may be, but not limited to, a bifurcated stent end having two hollow tubular structures at one of its ends.

In another aspect of the present invention, the interlaced adjacent cell segments are defined by at least one wire from one cell being knittingly interlaced with at least one wire from the adjacent cell.

In yet another aspect of the present invention the perimetrically bound cells have a polygonal configuration. Useful polygonal configurations include, but are not limited to, three-sided to twelve-sided configurations. A substantially hexagonal configuration and a substantially diamond-shaped, four-sided configuration are preferred examples of useful polygonal configurations.

In still another aspect of the present invention, the stent is a radially expandable stent. Desirably, the stent is formed from a wire of a shape memory material. One useful shape memory material is a nickel titanium alloy. Alternately or additionally, the wire may be formed from a biocompatible material.

In another embodiment of the present invention, a knitted implantable stent including a hollow tubular structure having opposed open ends defining a wall portion therebetween; the wall portion including an open lattice structure of a plurality of interconnected perimetrically bound cells; the cells defined by a plurality cell segments; wherein the cell segments include an elongate wire knitted interlaced into a plurality of loops and wherein the elongate wire from one cell segment of one cell is knittingly interlaced with the elongate wire from one cell segment of an adjacent polygonal cell to the open lattice structure of interconnected perimetrically bound cells is provided. This stent may be a singular tubular structure or may be, but not limited to, a bifurcated stent end having two hollow tubular structures at one of its ends.

The stent of this second embodiment may also have its perimetrically bound cells in the above-mentioned polygonal configurations, such as from three-sided to twelve-sided configurations, including a substantially diamond-shaped, four-sided configuration.

The stent of this second embodiment may also be a radially expandable stent, desirably formed from a shape memory material, such as a nickel titanium alloy. A biocompatible material may also be suitably used to form the stent of this embodiment.

In another embodiment of the present invention, a flat-knitted implantable stent including a first elongate wire interlaced with a second elongate wire in a knitted pattern to form an elongate, hollow and cylindrical stent having an open mesh wall portion; wherein the open mesh wall portion is an open lattice structure of interconnected perimetrically bound cells defined by the interlaced wires in the knitted pattern and wherein the knitted-pattern is a warp knitted pattern produced on a double needle bar knitting machine is provided.

A method for producing a stent includes the steps of providing at least two elongate wires; flat-knitting the wires to form a plurality of cell segment all of which having a plurality of loops; flat-knitting the cell segments to form an open lattice structure having a plurality of perimetrically bound cells; and flat-knitting wires from one cell segment to knittingly interlace wires from another cell segment interconnect adjacent perimetrically bound cells to define a hollow tubular structure having opposed open ends defining a wall portion therebetween.

The method may further include the step of selecting a knitting machine for flat-knitting the wires. Desirably, the knitting machine is a double needle bar knitting machine. More desirably, the knitting machine is a double needle bar raschel knitting machine.

The method may further include the step of positioning the stent over an elongate cylindrical mandrel; and heat setting the stent to provide a substantially cylindrical hollow tubular structure.

The stents of the present invention may further include a tubular graft circumferentially positioned internally or externally to the wall portion of the stent, wherein the graft is a textile graft, a polymeric graft, and combinations thereof to provide a stent-graft endoprosthesis. The textile graft may a knitted graft, a woven graft or a braided graft. A useful polymeric graft includes an expanded polytetrafluoroethylene graft.

BRIEF DESCRIPTION OF THE DRAWINGS

FIG. 1 is a perspective view of the knitted open lattice stent of the present invention.

FIG. 2 is a cross sectional view of the stent of FIG. 1 taken along the 2—2 axis having a substantially circular cross sectional area.

FIG. 3 is a cross sectional view of the stent of FIG. 1 in its flat knitted shape prior to processing the stent into a circular cross sectional area.

FIG. 7 depicts a portion of the stent of FIG. 1 having another alternate knitted pattern of interlacing wires.

FIG. 8 depicts a portion of cell structure of the stent of FIG. 1 having a knitted pattern of interlacing wires in an open pillar stitch.

FIG. 9 depicts a portion of cell structure of the stent of FIG. 1 having a knitted pattern of interlacing wires in a closed pillar stitch.

FIGS. 12A and 12B depict a flat knitted bifurcated stent of the present invention.

FIG. 13 schematically depicts the placement of the stent of FIG. 1 onto a mandrel to set its circular shape.

DETAILED DESCRIPTION OF THE INVENTION

Figure 4A:
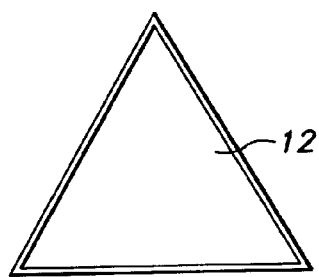
FIGS. 4A through 4J depict nonlimiting examples of polygonal shaped cells defining the open lattice structure of the stent of FIG. 1.
Figure 4F:
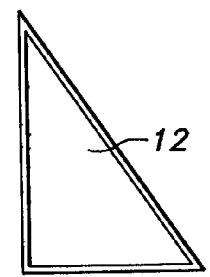
Figure 4B:
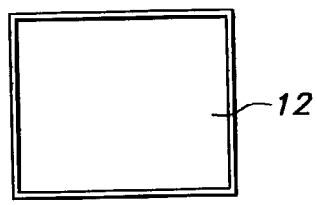
Figure 4G:
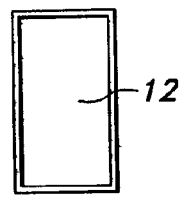
Figure 4C:
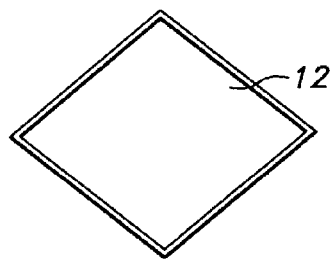

The present invention is a flat-knitted stent which addresses the problems associated with prior art stents. For example, the stent of the present invention has a unitary, open lattice structure without the disadvantages of the prior art, such as welding different stent segments to form a unitary structure. The flat knitted stents of the present invention also have enhanced flexibility and easier manufacturing techniques as compared to the stents of the prior art. The flat-knitted stents of the present invention may be suitably produced on a commercial knitting machine, such as double needle bar raschel knitting machine. Flat-knitted stents have a substantially flat shape, for example stent 10 as depicted in FIG. 3, as produced by a noncircular or flat knitting machine, such as a double needle bar flat-knitting machine, and are subsequently formed into substantially cylindrical structures with a generally circular cross section as described below.

FIG. 1 is a perspective view of stent 10 of the present invention. Stent 10 is a hollow tubular structure with an open lattice structure. The open lattice structure is defined by a plurality of polygonal cells, such as cells 12 and 14. The polygonal cells are defined by cell segments. For example, polygonal cell 12 is depicted as a hexagonal with six cell segments 16, 18, 20, 22, 24 and 26. Certain cell segments, such as cell segment 24, join cell 12 and cell 14 to one and the other.

FIG. 2 is a cross sectional view of stent 10 taken along the 2—2 axis. The open lattice cell structure with adjacent cells, such as cells 12 and 14, being joined together form a wall portion 28 of generally circular cross section, as depicted in FIG. 2. The stent 10 is a hollow tubular structure having a generally elongate cylindrical shape with a substantially circular diameter for placement within a bodily lumen.

Figure 4H:
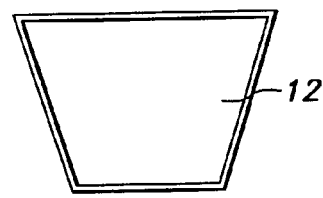
Figure 4D:
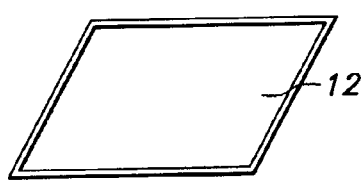
Figure 4I:
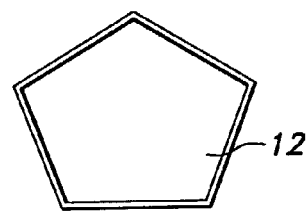
Figure 4E:
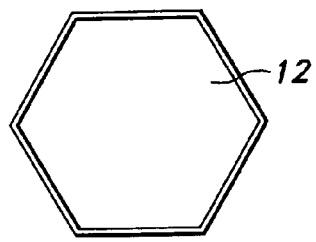
Figure 4J:
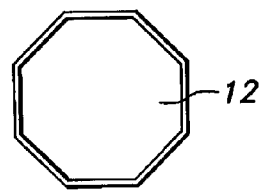

Although cell 12 is depicted as a generally hexagonal cell in FIG. 1, the present invention is not so limited. Cell 12 may suitably be any useful geometric shape, such as any three- to twelve-sided polygonal cells, some of which are depicted in FIGS. 4A through 4J, having a variety of different cell orientations. For example, cell 12 having four cell segments may be squared shape (FIG. 4B), rectangularly shaped (FIG. 4G), diamond shaped (FIG. 4C) or other shapes not having segments at ninety degree angles as depicted in FIGS. 4D and 4H. Moreover, the cell segments are not limited to segments of straight lines. The segments may be slightly curved, especially at points of intersection or change in direction. For example, cell segments 22 and 23 may be curved at their point of intersection 25. Thus, as used herein, the term "polygonal" and its variants refer to a geometric shape formed from three to twelve segments in a perimetrically bound relationship where the segments may be substantially straight or may be curved. Furthermore, cell 12 need not even be a polygonal shaped cell, but any useful open cell shape, for example circular or elliptical, may suitably be used.

The cell segments are formed from elongate wires knittingly interlaced in a plurality of loops. Adjoining or adjacent cell segments are also knittingly interlaced to form perimetrically bound cells for the open lattice structure of the stent of the present invention. A nonlimiting example of a knitting pattern useful with the practice of the present invention is depicted in FIG. 5.

Wires 40 and 42 are knittingly interlaced to form cell segment 24 which is an adjoining cell segment formed by adjacent cells 12 and 14. Cell segment 24 is shown as series of recrossing pillar stitches. Cell segment 22 is also formed by knittingly interlacing wires 40 and 42 in a different pattern, such as a pillar stitch pattern as depicted in FIG. 5. As depicted in FIG. 5, each cell segment has a plurality of wires that are knittingly interlaced in a plurality of loops. Such integration of wires from one cell segment to another cell segment and from one cell to another cell forms an open mesh tubular knitted structure of unitary construction. Unlike some stents of the prior art, cell segments of the present invention do not have to be welded together, or otherwise mechanically secured together, to form a unitary open lattice structure.

Figure 5:
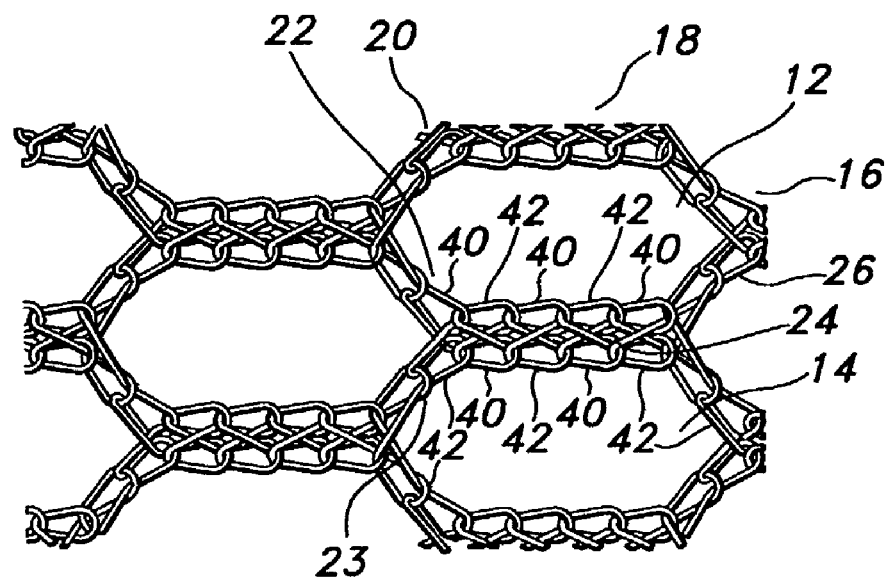
FIG. 5 depicts a portion of the stent of FIG. 1 having a knitted pattern of interlacing wires.
Figure 6:
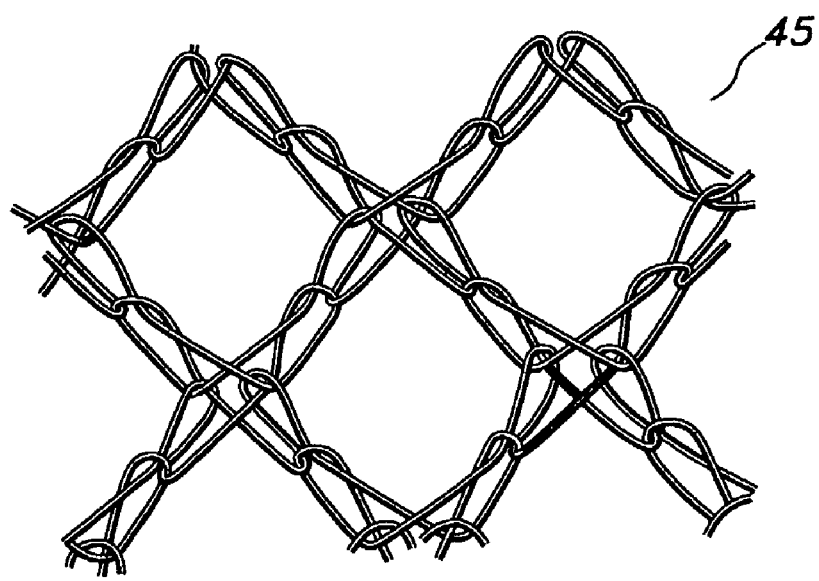
FIG. 6 depicts a portion of the stent of FIG. 1 having an alternate knitted pattern of interlacing wires.

The present invention is not, however, limited to the particular knitting patterns depicted in FIG. 5 and other pattern may suitably be used. For example, diamond shaped open meshed structures may also be flat-knitted as depicted in FIGS. 6 and 7. The length of the cell segment 45 may be increased by increasing the number of knitting stitches or loops in the segment, which is depicted as going from one loop in FIG. 7 to two loops in FIG. 6. The length of cell segments is not limited to one or two loops, but a plurality of open loops, where engaging wires do not cross over themselves, a plurality of closed loops, where the engaging wires cross over themselves, or combination thereof may suitably be used. Examples of open and closed loops are depicted in FIG. 8 (open pillar stitches) and FIG. 9 (closed pillar stitches).

Regardless of the type of interlacing knitting stitches in a cell segment, the plurality of such stitches advantageously provides greater flexibility to the stent of the present invention as compared to prior art stents, even prior art braided and prior art circular knitted stents. The enhanced flexibility is achieved, in part, by the having a cell segment that in itself is flexible due to its plurality of interlacing loops as compared to a cell segment of a single wire only interlacing at the terminus with another wire and not having intermediate interlacing loops within the cell segment itself.

The stents of the present invention are desirably formed from knitted wires. As used herein the term "wire" and its variants refer to an elongate filament of material having a substantially greater longitudinal dimension as compared to its thickness or diameter. As used herein, a wire need not have a circular cross section, but other cross sections such as elliptical or polygonal, may suitable be used. Desirably, however, wires of the present invention are substantially circular or elliptical in their cross sections. Moreover, as used herein, the term wire is not limited to elongate filaments of metallic substances. The wires may be made of polymeric materials. The wires are not, however, textile yarns or threads of either natural or synthetic materials.

Various stent constructions may be employed in the invention. Useful stents include, without limitation, self-expanding stents and balloon expandable stents. The stents may be capable of radially contracting or expanding, as well, and in this sense can be best described as radially or circumferentially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode, based on temperature. Other materials are of course contemplated, such as stainless steel, platinum, gold, titanium, tantalum and other biocompatible metals, including alloys, such as Elgiloy®, a Ni—Co—Cr-based alloy, as well as polymeric stents.

As used herein, the phrase "radially expandable stent" and it variants refer to a stent that is radially expandable from a quiescent state, or radially contractible from an expanded state to a quiescent state. Such radially expandable stents may be self-expanding or require mechanical means, such as inflation by a balloon catheter, for expanding. Desirably, radially expandable stents of the present invention do not exhibit substantial longitudinal changes, such as less than about 50 linear percent longitudinal change, during the radial expansion or contraction, due to their open mesh knitted configuration. More desirably, the radially expandable stents of the present invention exhibit less than about 20 linear percent longitudinal change, during the radial expansion or contraction, due to their open mesh knitted configuration.

Figure 10:
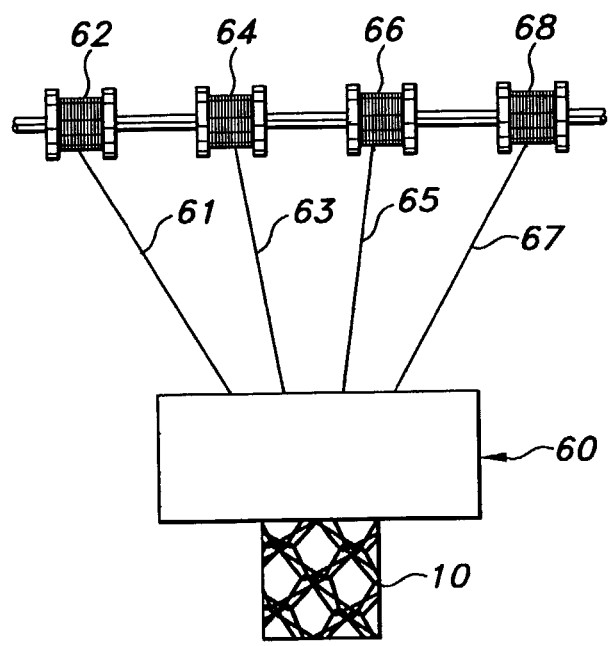
FIG. 10 schematically depicts a flat knitting for producing the stent of FIG. 1.

FIG. 10 is a schematic depiction of a knitting machine 60 useful for producing the flat-knitted stents of the present invention. The machine 60 is fed with wires 61, 63, 65, and 67 from spools 62, 64, 66, and 68, respectively. Machine 60 knits the wires 61, 63, 65, and 67 to form the stent 10. Machine 60 simultaneously knits the top portion 70 of stent 10 and the bottom portion 72 of stent 10. As depicted in FIG. 3, the top portion 70 and the bottom portion 72 have the configuration of generally flat elongate strips as produced on machine 60. The stent 10 is carried forward by a conveyor belt (not shown).

Wires 61 and 63 are processed by machine 60 into the top portion 70 of stent 10, and the wires 65 and 67 are similarly and simultaneously processed by machine 60 into the bottom portion 72 of stent 10. As the top portion 70 and the bottom portion 72 are warp-knitted by machine 60, the machine 60 also simultaneously knits the two portions together along the elongate edges thereof to join the portions as indicated by reference numbers 74 and 76 in FIG. 3.

Machine 60 can also knit a bifurcated stent 100 which is schematically illustrated in FIGS. 12A and 12B. Bifurcated stent 100 has a main tubular portion 102 and two tubular leg portions 104 and 106. Wires that form the main tubular portion 102 are split into separate knitted tubular patterns by control of wire guides (not shown) to knittingly produce the leg portions 104 and 106. The present invention, however, is not limited to single lumen or bifurcated stents and other shapes may be suitably formed on machine 60. For example, stent 10 or stent 100 may be suitably knitted where the wall portion has a varying diameter and/or shape. Also the legs 104 and 106 are not limited to substantially equal diameters or lengths as depicted in FIGS. 12A and 12B. The lengths and diameters of legs 104 and 106 can vary. Moreover, the knitting pattern can be altered along the length of any particular part of the stent to change the configuration of the open lattice structure. For example, the length, breath or even the geometric shape of open lattice structure can vary by changing the knitting pattern used to produce the various cells or cell segments.

Figure 11:
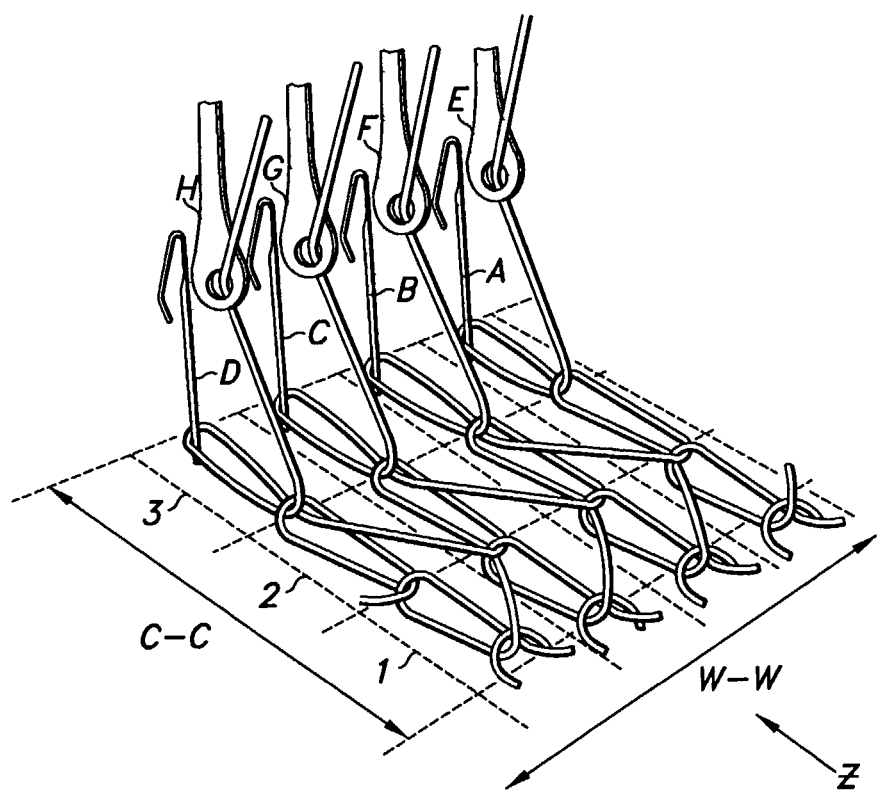
FIG. 11 depicts a portion of the flat knitting machine of FIG. 10 showing a needle bar and wire guides.

FIG. 11 depicts a portion of the machine 60. Needles A, B, C and D are arranged in an array often referred to as a needle bar. The needles A, B, C, and D may be simultaneously lapped by separate warp guides E, F, G and H. As the needles A, B, C and D receive their overlaps, a warp guide underlapping from one needle to another will be passing from one knitting cycle or course to the next. Different courses are indicated along the C—C vector and are indicated by courses 1, 2 and 3. The direction perpendicular to the courses and the knitted wires thereat are referred to as wales as indicated by vector W—W. The direction of knitting is indicated by the vector Z.

Desirably, machine 60 has two arrays of needles or two needle bars (not shown). Such a double needle bar knitting machine is often referred to as a double needle bar raschel knitting machine. Such double needle bar raschel knitting machines are available from Karl Mayer Textilmaschinenfabrik GmbH, Obertshausen, Germany. Such machines typically have the needle bars placed exactly behind each other for convenience of the guide bar operation and are referred to as a front needle bar and a back needle bar. Moreover, such knitting machines often has a plurality of guide bars to control the knitting pattern of the stent, for example guide bars controlling the top portion 70, the bottom portion 72 and the adjoining sections 74 and 76 of stent 10.

To achieve a general circular tubular shape, as depicted in FIG. 2, stent 10 is placed over a mandrel 80. As depicted in FIG. 13, mandrel 80 is an elongate cylindrical tubular member. Heat treatment methods may then be used to set the shape of the stent 10 that generally corresponds to the shape of the mandrel 80. When the stent 10 is made from shape memory materials, such as nickel-titanium shape alloys or nitinols, the heat treatment parameters may be chosen to set both the shape and the shape memory properties. A Non-limiting heat treatment for setting the shape includes heating the stent 10 to a first temperature from about 400° C. to about 500° C. for several minutes followed by cooling, which can be rapid via use of a quench. After cooling the stent is often reheated to a second temperature which is less than the first temperature to set the final shape of the stent. The stent 10 may be confined on the mandrel 80 during the heat treatment by any convenient means (not shown). Alternatively, a circular stent may be produced without confinement on a mandrel by allowing it to expand during the heat treatment process.

The heat treating of a stent made from shape memory or superelastic materials can set both the desired shape and temperature at which the stent will radially expand or contract. Examples of shape memory materials include, for example, nitinol, tantalum steel, stainless steel or other elastic metals, or certain plastics such as polyester, polypropylene, or carbon fiber. The stent wire is preferably made of an alloy of nickel and titanium which provides the stent with a thermal memory. The characteristics of such alloys which are generally known as nitinol is that they have thermally triggered shape memories which allow the stent to be constructed in a first condition, such as an expanded shape, and delivered into a bodily lumen in a compressed second condition. The stent then regains its memorized enlarged shape when warmed to a selected temperature such as human body temperature. The two interchangeable shapes sizes are possible because of the two different crystalline structures which exist in such alloys at different temperatures. The transition temperature range (TTR) is the temperature at which the stent changes its shape and the TTR can be controlled, in part, by the selection of particular ratio of metals in the alloy. Below the TTR the alloy is highly ductile and may be plastically deformed into a second desired shape. Upon reheating above the TTR the alloy returns to its first pre-set form.

Figure 14:
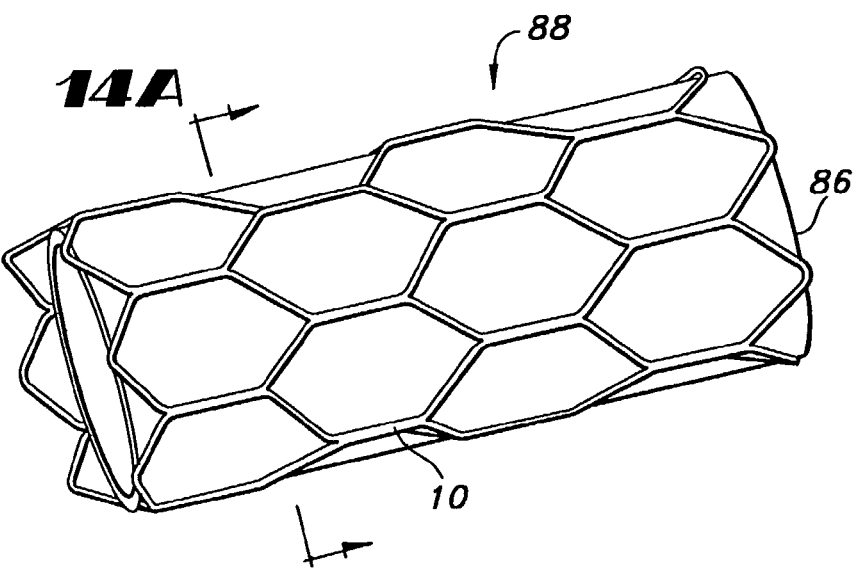
FIG. 14 depicts a stent-graft formed from the stent of FIG. 1.
Figure 14A:
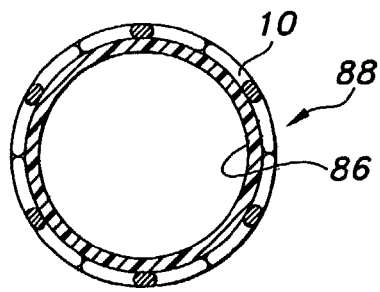
FIG. 14A is a cross sectional view of the stent-graft of FIG. 14 taken along the 14a—14a axis.
Figure 14C:
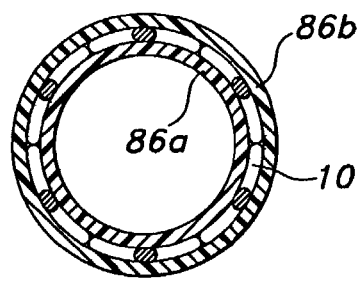
FIGS. 14B and 14C depict additional embodiments of the stent-graft of the present invention.
Figure 14B:
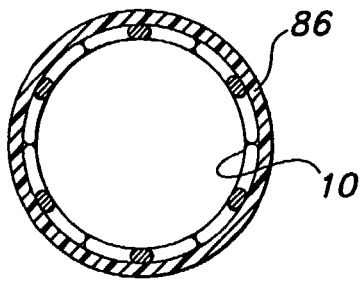

In another embodiment of the present invention, a stent-graft 88 is formed to provide a stent-graft endoprosthesis. As depicted in FIGS. 14 and 14A, graft 86 is circumferentially disposed within stent 10 to provide the stent-graft 88 of the present invention. As depicted in FIG. 14B, graft 86 may also be disposed around the exterior of stent 10. Furthermore, as depicted in FIG. 14C, the stent-graft may have an interiorly and exteriorly disposed grafts, such as grafts 86a and 86b.

Grafts are typically hollow tubular devices that may be formed of a variety of materials, including textile and non-textile materials. Non-textile materials, such as polymeric tubes or sheets, may suitably be used with the present invention. Expanded polytetrafluoroethylene or e-PTFE is one common polymeric material useful as the graft portion of a stent-graft endoprosthesis of the present invention. Typically, the non-textile grafts and the knitted stents of the present invention are formed by different techniques and on different equipment, followed by securing the graft to the stent by mechanical means, such as adhesive bonding, fusion bonding, suturing and the like.

PTFE exhibits superior biocompatibility and low thrombogenicity, which makes it particularly useful as vascular graft material in the repair or replacement of blood vessels. Desirably, the non-textile layer is a tubular structure manufactured from expanded polytetrafluoroethylene (ePTFE). The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Graft 86 may also be a tubular textile graft, such as a knitted graft which may be attached to the stent or even to another graft, such as an extruded ePTFE layer, by a number of means. For example, a tubular knitted graft may have a pattern of interlaced yarns arranged in a resilient knit pattern which permits longitudinal expansion or contraction consistent with the longitudinal expansion or contraction of the extruded ePTFE and/or stent. Although knitted textile grafts are desirable for use in conjunction with the present invention due to their ability to longitudinally expand, other textile patterns such as braided patterns or even expandable woven patterns, are also useful.

In order to achieve such a degree of longitudinal expansion or contraction the textile graft is desirably formed from a resilient knit pattern. In one aspect the resilient pattern is a warp knitted pattern having a yarn diagonally shifted over one or more yarns in the course direction to form a loop between engaging yarns. Furthermore, the engaging yarns alternately form open loops where engaging yarns do not cross over themselves and closed loops where engaging yarns cross over themselves. Such a resilient knit pattern is described as Atlas and modified Atlas knit patterns. Such patterns impart a high degree of flexibility and stretchability to the knitted textile graft. Such knit patterns are further described in the commonly assigned application titled "Low Profile, High Stretch Knit Prosthetic Device" (U.S. patent application Ser. No. 09/898,097, filed Jul. 3, 2001), which is herein incorporated by reference.

In another aspect the resilient pattern is a warp knitted pattern having sets of yarns diagonally shifted over two or more yarns before forming a loop between engaging yarns. Such a resilient pattern is a warp knit pattern with at least a two needle underlap. Such patterns impart a high degree of flexibility and stretchability to the textile graft, while also providing radially restricted enlargement to the knitted textile graft. Such knit patterns are further described in the commonly assigned application titled "Low Profile, High Stretch, Low Dilation Knit Prosthetic Device" (U.S. patent application Ser. No. 09/898,103, filed Jul. 3, 2001), which is herein incorporated by reference.

The above-described knitted textile graft are desirably made on a warp-knitting machine (not shown) using a double needle bar. Such grafts are typically flat knitted, similar to the flat knitting of the stent of the present invention. Desirably, the textile graft is a single layer construction so that the textile wall thickness is minimized to yield a low profile knitted textile graft. For example, a non-limiting textile wall thickness from about 0.3 to about 0.4 millimeters is useful with the present invention.

Any type of textile product can be used as yarns for the knitted textile graft. Of particular usefulness in forming the knitted fabric prosthesis of the present invention are synthetic materials such as synthetic polymers. Synthetic yarns suitable for use in the present invention include, but are not limited to, polyesters, including PET polyesters, polypropylenes, polyethylenes, polyurethanes and polytetrafluoroethylenes. The yarns may be of the monofilament, multifilament, spun type or combinations thereof. The yarns may also be flat, twisted or textured, and may have high, low or moderate shrinkage properties or combinations thereof.

The yarns used in forming the textile grafts may be flat, twisted, textured or combinations thereof. Furthermore, the yarns may have high, low or moderate shrinkage properties or combination of different shrinkage properties. Additionally, the yarn type and yarn denier can be selected to meet specific properties desired for the prosthesis, such as porosity and flexibility. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 200, preferably from about 30 to about 100. Preferably, the yarns are polyester, such as polyethylene terephthalate (PET), and more preferably the yarns are one ply, 40 denier, 27 filament flat and texturized polyester.

A useful, non-limiting number of needles per inch for warp knitting is from about 18 to about 36. Furthermore, the knitted textile grafts generally have greater than 2,000 stitches per square inch, for instance from about 2,600 to about 6,500 stitches per square inch, to provide compliancy of the graft.

Figure 15:
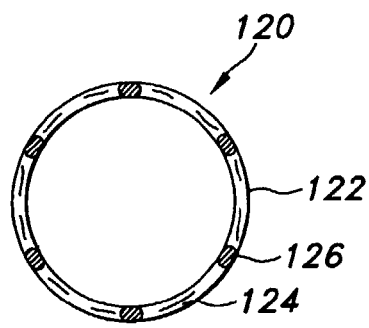
FIG. 15 depicts a stent-graft of the present invention formed from knittingly interlacing stent-forming wires and graft-forming textile yarns.

Moreover, the flat knitted stent of the present invention may be co-knitted with the above-described flat knitted textile grafts. In other words, a knitted stent-graft can be suitably produced as an unitary structure on the same knitting machine. Selective textile yarns from the textile graft may be knittingly interlaced with selective wires from the knitted stent to form such a unitary structure. Such a co-knitted stent-graft 120 is depicted in FIG. 15, where wall 122 of the co-knitted stent-graft 120 is formed from a combination of textile graft yarns 124 and stent wires 126.

Although illustrative aspects of the present invention have been described herein with reference to the accompanying drawings, it is to be understood that the invention is not limited to those precise aspects, and that various other changes and modifications may be effected therein by one skilled in the art without departing from the scope or spirit of the invention.

What is claimed is:

1. A knitted implantable stent comprising:
a hollow tubular structure having opposed open ends defining a wall portion therebetween; the wall portion comprising an open lattice structure of a plurality of interconnected perimetrically bound cells; the cells defined by a plurality of cell segments;
wherein the cell segments are defined by at least two wires knittingly interlaced in a plurality of loops selected from the group consisting of open pillar stitches, closed pillar stitches or combinations thereof and wherein adjacent cell segments are knittingly interlaced with each other to form the open lattice structure of interconnected perimetrically bound cells.

2. The stent of claim 1, wherein the interlaced adjacent cell segments are defined by at least one wire from one cell being knittingly interlaced with at least one wire from the adjacent cell.

3. The stent of claim 1, wherein the perimetrically bound cells have a polygonal configuration.

4. The stent of claim 3, wherein the polygonal configuration is from a three-sided to a twelve-sided configuration.

5. The stent of claim 3, wherein the polygonal configuration is a substantially hexagonal configuration.

6. The stent of claim 3, wherein the polygonal configuration is a substantially diamond-shaped, four-sided configuration.

7. The stent of claim 1, wherein the stent is a radially expandable stent.

8. The stent of claim 7, wherein the wire is formed from a shape memory material.

9. The stent of claim 8, wherein the shape memory material is a nickel titanium alloy.

10. The stent of claim 1, wherein the wire is formed from a biocompatible material.

11. The stent of claim 1, wherein one of the open ends is a bifurcated end having two hollow tubular structures.

12. The stent of claim 1, further comprising a tubular graft circumferentially positioned internally or externally to the wall portion of the stent, wherein the graft is a textile graft, a polymeric graft, and combinations thereof.

13. The stent of claim 12, wherein the textile graft is a knitted graft, a woven graft or a braided graft.

14. The stent of claim 12, therein the polymeric graft is an expanded polytetrafluoroethylene graft.

15. The stent of claim 1, further comprising textile yarns knittingly interlaced to form a textile graft, wherein a portion of the yarns from the textile graft are knittingly interlaced with a portion of the wires from the stent to form a unitary structure.

16. A knitted implantable stent comprising:
a hollow tubular structure having opposed open ends defining a wall portion therebetween; the wall portion comprising an open lattice structure of a plurality of interconnected perimetrically bound cells; the cells defined by a plurality cell segments;
wherein the cell segments comprise at least two elongate wire knittingly interlaced into a plurality of loops selected from the group consisting of open pillar stitches, closed pillar stitches or combinations thereof and wherein the elongate wire from one cell segment of one cell is knittingly interlaced with the elongate wire from one cell segment of an adjacent polygonal cell to the open lattice structure of interconnected perimetrically bound cells.

17. The stent of claim 16, wherein the perimetrically bound cells have a polygonal configuration.

18. The stent of claim 16, wherein the polygonal configuration is from a three-sided to a twelve-sided configuration.

19. The stent of claim 16, wherein the polygonal configuration is a substantially diamond-shaped, four-sided configuration.

20. The stent of claim 16, wherein the stent is a radially expandable stent.

21. The stent of claim 16, wherein the wire is formed from a shape memory material.

22. The stent of claim 21, wherein the shape memory material is a nickel titanium alloy.

23. The stent of claim 22, wherein the wire is formed from a biocompatible material.

24. The stent of claim 16, wherein one of the open ends is a bifurcated end having two hollow tubular structures.

25. The stent of claim 16, further comprising a tubular graft circumferentially positioned internally or externally to the wall portion of the stent, wherein the graft is a textile graft, a polymeric graft, and combinations thereof.

26. The stent of claim 25, wherein the textile graft is a knitted graft, a woven graft or a braided graft.

27. The stent of claim 25, therein the polymeric graft is an expanded polytetrafluoroethylene graft.

28. The stent of claim 16, further comprising textile yarns knittingly interlaced to form a textile graft, wherein a portion of the yarns from the textile graft are knittingly interlaced with a portion of the wires from the stent to form a unitary structure.

29. A flat-knitted implantable stent comprising:
a first elongate wire interlaced with a second elongate wire in a knitted pattern to form an elongate, hollow and cylindrical stent having an open mesh wall portion;
wherein the open mesh wall portion is an open lattice structure of interconnected perimetrically bound cells defined by the interlaced wires in the knitted pattern and wherein the knitted-pattern is a warp knitted pattern selected from the group consisting of open pillar stitches, closed pillar stitches or combinations thereof and is produced on a double needle bar knitting machine.

30. A method for producing a stent comprising:
providing at least two elongate wires;
flat-knitting the wires to form a plurality of cell segment all of which having a plurality of loops selected from the group consisting of open pillar stitches, closed pillar stitches or combinations thereof;
flat-knitting the cell segments to form an open lattice structure having a plurality of perimetrically bound cells; and
flat-knitting wires from one cell segment to knittingly interlace wires from another cell segment interconnect adjacent perimetrically bound cells to define a hollow tubular structure having opposed open ends defining a wall portion therebetween.

31. The method of claim 30, further comprising selecting a knitting machine for flat-knitting the wires.

32. The method of claim 31, wherein the knitting machine is a double needle bar knitting machine.

33. The method of claim 31, wherein the knitting machine is a double needle bar raschel knitting machine.

34. The method of claim 30 further comprising:
positioning the stent over a elongate cylindrical mandrel; and
heat setting the stent to provide a substantially cylindrical hollow tubular structure.

35. The method of claim 30 further comprising:
providing textile yarns;

flat-knitting the textile yarns to form a textile graft portion; and
knittingly interlacing a portion of the textile yarns with a portion of the wires to form a unitary structure.

\* \* \* \* \*

UNITED STATES PATENT AND TRADEMARK OFFICE
CERTIFICATE OF CORRECTION

PATENT NO. : 7,011,676 B2  Page 1 of 1
APPLICATION NO. : 10/235447
DATED : March 14, 2006
INVENTOR(S) : Dong, Q.

It is certified that error appears in the above-identified patent and that said Letters Patent is hereby corrected as shown below:

At column 1, line 55, the printed patent should read "...a stent may be made from a..""".

At column 2, line 10, the printed patent should read "...for forming the stent.".

At column 2, line 34, the printed patent should read "...the stent from the mandrel,...".

At column 2, lines 55-56, the printed patent should read "...so that the configuration can be somewhat...".

At column 3, line 13, the printed patent should read "...defined by a plurality of cell segments.".

At column 3, line 44, the printed patent should read "..defined by a plurality of cell segments.".

At column 4, lines 29-30, the printed patent should read "...graft may be a knitted graft,...".

At column 8, line 19, the printed patent should read "...machines often have a plurality of...".

Signed and Sealed this

Eleventh Day of July, 2006

JON W. DUDAS
*Director of the United States Patent and Trademark Office*